United States Patent [19]

Young et al.

[11] Patent Number: 4,881,299

[45] Date of Patent: Nov. 21, 1989

[54] ORTHOPAEDIC AND ORTHOTIC BI-PIVOTAL HINGE WITH IMPROVED ADJUSTMENT MEANS

[76] Inventors: David E. Young, Bowler's Piece, 16 Couching Street, Watlington, Oxon, England, OX9 5QQ; Kenneth P. Davis, 7 Dean Close, Hillingdon, Middlesex, England, UB10 9LB

[21] Appl. No.: 156,250

[22] Filed: Feb. 16, 1988

[30] Foreign Application Priority Data

Feb. 18, 1987 [GB] United Kingdom ............... 8703823

[51] Int. Cl.$^4$ ............................................. E05D 11/06
[52] U.S. Cl. ........................................... 16/371; 128/88; 128/80 C; 16/375; 16/239
[58] Field of Search ............... 128/80 C, 88, 80 F, 128/80 H, 80 R, 80 B, 80 J, 89 R, 89 A; 623/39; 16/368, 371, 375, 235, 239

[56] References Cited

U.S. PATENT DOCUMENTS

| | | | |
|---|---|---|---|
| 2,573,866 | 11/1951 | Murphy | 128/80 F |
| 2,632,440 | 3/1953 | Hauser et al. | 128/80 F |
| 3,350,719 | 11/1967 | McClure | 2/22 |
| 3,552,786 | 1/1971 | Schmid | 287/100 |
| 3,958,569 | 5/1976 | Vosburgh | 128/80 C |
| 4,245,629 | 1/1981 | Cummins | 128/80 C |
| 4,249,524 | 2/1981 | Anderson | 182/80 C |
| 4,323,059 | 4/1982 | Rambert et al. | 128/80 C |
| 4,337,764 | 6/1982 | Lerman | 128/80 F |
| 4,370,977 | 2/1983 | Mauldin et al. | 128/80 F |
| 4,397,308 | 8/1983 | Hepburn | 128/80 F |
| 4,407,276 | 10/1983 | Bledsoe | 128/80 C |
| 4,489,718 | 12/1984 | Martin | 128/80 C |
| 4,493,316 | 1/1985 | Reed et al. | 128/88 |
| 4,502,472 | 3/1985 | Pansiera | 128/80 F |
| 4,520,802 | 6/1985 | Mercer et al. | 128/80 C |
| 4,538,600 | 9/1985 | Hepburn | 128/88 |
| 4,599,998 | 7/1986 | Castillo | 128/77 |
| 4,620,532 | 11/1986 | Houswerth | 128/80 C |

FOREIGN PATENT DOCUMENTS 2182714 5/1987 United Kingdom ............... 128/88

OTHER PUBLICATIONS

PCT Published International Application (Anderson) WO82/02658.
European Published Application (Lerman) 0 059 472.
UK Published Application (Young et al.) 2 182 714A.

Primary Examiner—Edgar S. Burr
Assistant Examiner—Houng Q. Pham
Attorney, Agent, or Firm—Tilton, Fallon, Lungmus & Chestnut

[57] ABSTRACT

An orthopaedic and orthotic bi-pivotal hinge assembly having a hinge body and a pair of coplanar and independently-pivotal hinge arms. The proximal end portions of the hinge arms are disposed within the hinge body and have planar abutment surfaces that face in the same direction and are disposed immediately adjacent each other when the arms are in full extension. Continuously variable extension control is achieved by an adjuster screw carried by the hinge body that is engageable with both of said planar abutment surfaces of said arms.

8 Claims, 2 Drawing Sheets

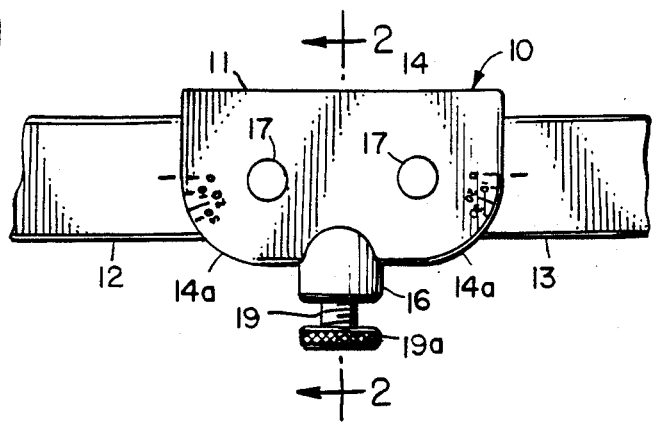
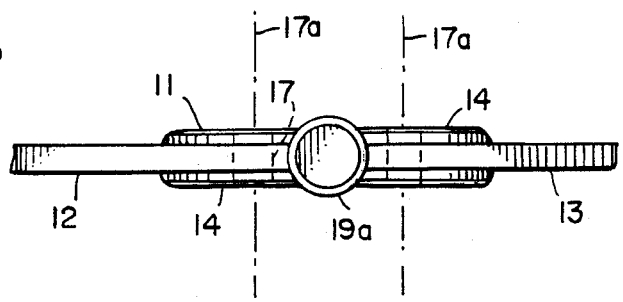
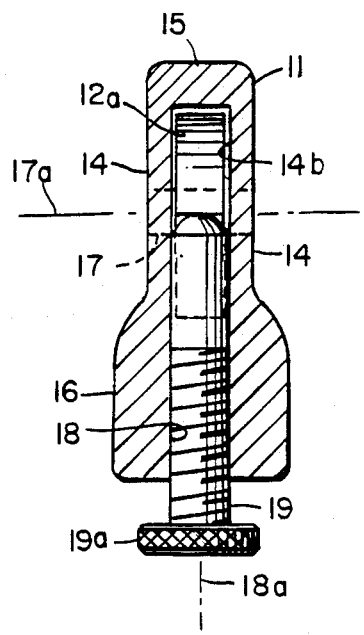

ORTHOPAEDIC AND ORTHOTIC BI-PIVOTAL HINGE WITH IMPROVED ADJUSTMENT MEANS

FIELD OF THE INVENTION

The present invention relates generally to bipivotal orthopaedic and orthotic hinge mechanisms or assemblies which are used in braces of various kinds.

Orthopaedic and orthotic hinges vary considerably in design and function. They are employed at joints, such as the knee or elbow, and their function is usually to supplement or partially substitute for the weight-bearing and motional characteristics of these joints. They are generally used in pairs with one hinge fitted laterally and the other fitted medially across the joint.

Orthopaedic and orthotic hinges are of two main types. The first employs a single pivot and is generally described as uniaxial or unipivotal; this type is quite commonly used in knee braces fitted in the practice of sports medicine, often following damage to the ligaments of the knee. Uniaxial hinges have also been used in lower leg walking devices for fractures of the foot. Such devices are used instead of short leg walking casts. In biomechanical terms, single pivot hinges are unphysiological when used at the knee because the knee does not move as a simple pivot hinge.

The second type of hinge mechanism has a central mount or hinge body which bears two pivots. The hinge arms are mounted one on each pivot and may either be independently pivotal or interconnected by gear teeth for coordinated pivotal action. In mechanical terms, a geared two pivot mechanism loses one degree of freedom when compared with two pivots which are not geared together. Geared two pivot hinges are also unphysiological when used at the knee because they effectively offer a single pivot point which migrates rearwardly when the hinge is moved from fully extended to fully flexed condition.

Two pivot hinge mechanisms in which the pivots or hinge arms are not geared together but are independently pivotal with respect to the hinge body may be called true bi-pivotal hinges, or by some authors, true bi-axial hinges. They are considered to offer good tracking of the human knee joint as the femoral condyles glide over the tibial plateau when the leg is extended from a fully flexed position. Such a hinge assembly may be provided with a stop for preventing hyperextension of the hinge arms.

We know of few commercially available examples of true bi-pivotal hinges and have found relative few references in the published art. One construction is believed to be based on Anderson U.S. Pat. No. 4,249,524 and published International Application WO 82/02658 (published Aug. 19, 1982). While the U.S. patent discloses a bi-pivotal hinge, it is believed that such hinge has unphysiological operating characteristics. The pivots are widely spaced to an extent that would tend to produce a pistoning action of the joint or limb in relation to the orthosis, an action that is undesirable especially in a damaged knee or in a knee which has recently undergone surgical repair or in a leg where there is a fracture. In the published International Application, the hinge differs as far as terminations of the hinge bars are concerned, but the drawings still reveal widely-separated pivots. Although Anderson briefly mentions stops in the published application, there is no disclosure of a variable motion limiting system.

In U.S. Pat. No. 4,337,764 and published European patent application No. 821015955, Lerman discloses an adjustment mechanism for two-pivot geared hinges. The system depends on a hinge backplate with an arcuate slot in which there are located two compression screw sets lying outside either side of the hinge arm. Since the hinge arms are geared together and cannot move independently, the disclosed construction is not a true bi-pivotal hinge.

U.S. Pat. No. 4,520,802 to Mercer and Aaserude discloses another bi-pivotal hinge featuring wide pivot spacing. The disclosure includes a motion control system based on indexing blocks. The system is discontinuous and incapable of infinite variable adjustment, leaving the user subject to the values of the index blocks made available by the manufacturer.

Most hinges have securing means for fixing them directly or indirectly to a limb. Where a hinge mechanism is to be retained on the limb by a cast, it will usually have hinge arms which terminate in structures adapted for embedding in the cast and commonly termed headplates or anchor plates. Orthotic hinges are normally supplied as independent units which are subsequently either built directly onto plastic orthoses or fitted to mating side arms called "steels" and then incorporated into calipers. Lower limb orthoses in particular are generally secured to the limb with straps.

Observations made under widely varying conditions in several different countries lead us to the conclusion that strap-on devices have more potential for relative motion between limb and device than do casts. This is primarily because casts are inherently rigid and constitute a fully circumferential integrated structural unit, whereas strap-on devices are usually made from a combination of soft goods and flexible materials and cannot form an integrated circumferential structure. We believe, therefore, that in the design of motion control mechanisms for orthopaedic and orthotic hinges, adjustment systems should be capable of continuous or infinite variation between adjustment extremes. This ensures the proper compensation for relative motion between the leg and the brace when such hinges are used with strap-on braces can be achieved.

Other authors have described means for limiting motion in orthopaedic hinges but all too frequently the type of hinge selected is unsuitable for the joint being braced, especially when complex motion is involved such as that of the knee joint. Thus, the motion control mechanism in Houswerth U.S. Pat. No. 4,620,532 has the advantage of compactness but the uniaxial hinge is not well suited for knee bracing because no uniaxial hinge is known to track the human knee satisfactorily. In Castillo U.S. Pat. No. 4,599,998, the motion control system involves a ratchet and is also compact but is applied to a geared two-pivot system which again has known disadvantages in properly tracking the human knee.

Another type of adjustment mechanism for a two-pivot geared hinge is found in a construction marketed by Rolyan Manufacturing Co., Menomonee Falls, Wis., U.S.A. Two screws located in the top of the hinge body are used to limit travel of one hinge arm in flexion and extension, respectively. This is achieved by driving the screws down into the body so that the ends strike the top edges of the hinge arms. The screws remain exposed at all times and require a locking nut to maintain adjustment.

In our co-pending British patent application No. 8510028, published May 20, 1987 as GB No. 2,182,714A, and U.S. patent application Ser. No. 853,962, filed Apr. 21, 1986, we disclose a true bi-pivotal knee hinge which employs closely-spaced pivots. Each hinge arm includes a carrier with two cam abutment stops arising from it, one on either side of and close to its pivot. Motion limiting screws, one to control flexion and the other to control extension, are provided for each pivot.

Other patents representing the state of art are U.S. Pat. Nos. 3,350,719, 4,407,276, 3,958,569, 4,370,977, 4,489,718, 4,323,059, 3,552,786 and 4,502,472.

SUMMARY OF THE INVENTION

An important aspect of this invention lies in providing an orthopaedic and orthotic hinge mechanism that has all of the functional advantages of a true bi-pivotal hinge mechanism but, in contrast to prior constructions, is provided with locking means that is relatively uncomplicated and compact in construction and that may be readily adjusted for reliably controlling the maximum degree of extension of the hinge. Because of its relatively low profile (lateral-medical dimension), the hinge assembly is particularly useful for so-called functional or sports braces and for calipers.

The objects of this invention are accomplished by providing a hinge mechanism with one set of stops for blocking extension, one stop on each hinge arm, continuously variable over a useful clinical range by means of a single adjusting screw. Such mechanism provides extension blocking without risk of loss of adjustment at maximal physiological loads and is particularly suitable for functional knee braces used in the treatment of damaged and repaired knee ligaments.

Briefly, the adjustable bi-pivotal orthopaedic hinge assembly includes a hinge body having a pair of side plates with spaced, opposing inner surfaces. First and second hinge arms have their adjacent end portions received between the opposing inner surfaces of the side plates, and pivots connect the hinge arms and the hinge body for independent pivotal movement of the arms between flexion and extension. Each of the adjacent end portions of the arms has a planar abutment surface lying in a plane that is parallel with the pivot axes of the arms. The abutment surfaces of the two arms face in the same direction, are coplanar, and are disposed immediately adjacent each other to provide, in effect, a continuous planar surface, when the arms are in 180 degree alignment—that is, when the arms are in positions of full extension.

The hinge body also includes a screw housing having a threaded bore oriented so that its axis is equidistant from the pivot axes of the arms and is normal to the common plane of the abutment surfaces when the arms are in positions of full extension. An adjuster screw is threadedly received in the bore and is engagable with both of the abutment surfaces for selectively limiting the maximum extension of the arms. Ideally, the common plane of the abutment surfaces extends through both of the pivot axes when the arms are in full extension. If desired, a follower may be interposed between the adjuster screw and the abutment surfaces so that rotational forces of the screw are not applied directly against such abutment surfaces.

When the hinge assembly is used in a knee orthosis, the assembly is oriented so that the screw housing and the adjuster screw received in it extend posteriorly. The side plates may be joined posteriorly by the screw housing and anteriorly by an anterior wall or connecting plate. Goniometric markings may be provided on the outwardly-facing surface of one of the side plates of the hinge body to indicate the adjustment setting of the extension position of the assembly.

Other features, advantages, functions, and objects of the invention will become apparent from the specification and drawings.

DRAWINGS

FIG. 1 is a side view of a hinge assembly embodying this invention.

FIG. 2 is an enlarged cross-sectional view taken along line 2—2 of FIG. 1.

FIG. 3 is a posterior view of the assembly.

DETAILED DESCRIPTION OF PREFERRED EMBODIMENTS

Figure 4:
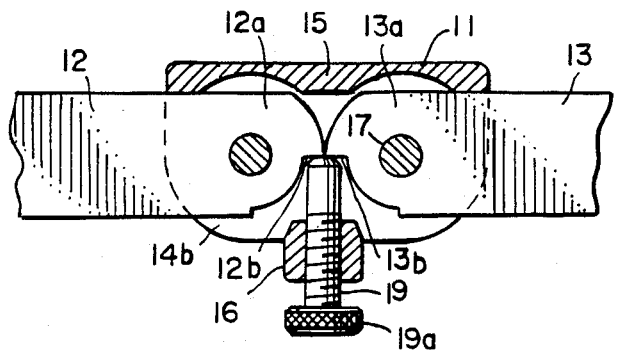
FIG. 4 is a sectional view of the assembly with the screw mechanism set in a position of full extension.

Referring to the drawings, the numeral 10 generally designates a hinge assembly that includes a hinge body 11 and a pair of hinge arms 12 and 13. The hinge body includes a pair of side plates 14 joined by an anterior wall or front plate 15. The posterior corners of the side plates are rounded at 14a and an enlarged boss or housing 16 joins the posterior portions of the side plates. As shown most clearly in FIG. 2, the housing 16, anterior wall 15, and side plates 14 may be integrally formed. Alternatively, such parts may be formed separately and secured together by any suitable means. The hinge body may be formed of any suitable material having sufficient strength and rigidity. Metals such as steel, titanium, and aluminum are appropriate, but high-strength rigid plastics may also be used.

Side plates 14 have opposing planar inner surfaces 14b that are spaced apart to receive the adjacent or proximal ends 12a and 13a of hinge arms 12 and 13 therebetween. Except in the respects described below, the hinge arms 12 and 13 are conventional, being formed of flat strips or bars of steel, aluminum, or other rigid materials having similar properties. The distal ends of the arms (not shown) are suitably adapted to fit headplates (as shown, for example, in U.S. Pat. Nos. 4,559,935 and 4,467,792), brace plates, or other known means for securing such arms to the limb of a patient. Since the hinge arms are formed of flat stock, the opposite side surfaces of proximal end portions 12a and 13a are planar, parallel to each other, and disposed in close proximity, and in opposing relation, to the inner surfaces 14b of side plates 14.

The proximal end portions 12a and 13a of the hinge arms are pivotally connected to the hinge body by means of pivot shafts or inserts 17 carried by side plates 14. As shown in FIG. 3, the shafts 17, and hence the pivot axes 17a of hinge arms 12 and 13, are parallel and extend in directions normal to the planes of side plates 14. The shafts 17 extend through the proximal end portions of the hinge arms and support the arms for independent pivotal movement between positions of flexion and extension.

Each of the proximal end portions 12a and 13a has a planar abutment surface 12b and 13b that is parallel with the pivot axes. As shown most clearly in FIG. 4, the two abutment surfaces face in the same direction towards housing 16, and are coplanar with each other, when the hinge arms 12, 13 are in full extension. Of particular importance is the fact that abutment surfaces 12b and 13b are disposed immediately adjacent each other so that together they form a nearly continuous planar surface when the arms are so extended.

Housing 16 has a threaded bore 18 with an axis 18a that is equidistant from pivot axes 17a and is also equidistant from the opposing surfaces 14b of the side plates with which it is parallel. Adjustment means in the form of an adjuster screw 19 is threadedly received in bore 18. The inner end of the screw is engagable with abutment surfaces 12b and 13b to limit the degree of extension of the arms 12 and 13. It will be seen that axis 18a (which is also the axis of adjustment screw 19) extends between the end portions 12a and 13a of the hinge arms and is normal to the common plane of abutment surface 12b and 13b when arms 12 and 13 are in positions of full extension, that is, when the arms are aligned at 180 degrees (FIG. 4). As the adjuster screw is driven inwardly, it blocks the hinge arms from reaching positions of full extension. The extension-blocking capability is infinitely variable between positions of full extension and of partial extension. The usual amount of extension blocking that would be imparted to preferred embodiments of the hinge would be approximately 60 degrees which exceeds the normal range of extension blocking employed following repairs to the cruciate ligaments of the knee.

Figure 5:
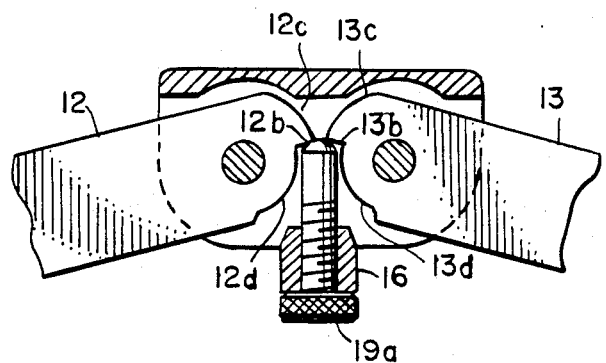
FIG. 5 is a sectional view similar to FIG. 4 but showing the screw mechanism set at a position of less than full extension.
Figure 6:
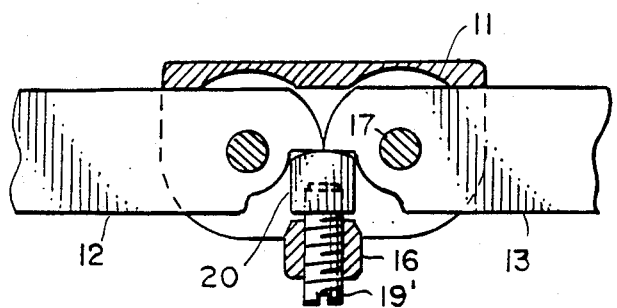
FIG. 6 is an enlarged fragmentary sectional view depicting a second embodiment of the invention.

Screw 19 may be provided with a head or cap 19a (FIGS. 1-5) or may be headless as depicted in FIG. 6. Since the adjuster screw 19 and screw housing 16 are disposed on the posterior or backside of hinge body 11, and since the axis of the screw is equidistant from pivot axes 17a, such elements would not be expected to contact the leg of a wearer (or other persons or objects) during normal use of the hinge assembly.

The proximal end portions of hinge arms 12 and 13 are provided with arcuate surfaces 12c, 12d, and 13c, 13d, to permit pivotal movement of the hinge arms without objectionable interference from the hinge body. Preferably, the inner end of adjuster screw 19 is rounded or chamfered to ensure effective engagement with abutment surfaces 12b and 13b when the adjuster screw is set to prevent full extension of the hinge arms (FIG. 5).

In a preferred embodiment of the invention, adjuster screw 19 may have a diameter of 6 mm with a 1 mm pitch. Applying such proportions to the embodiment illustrated, there would never be less than about 8 mm of thread in the bore 18 of housing 16; hence, the load transmitted from the abutment surfaces of the hinge arms would never be distributed over a thread length of less than:

$$8\pi = 150.9 \text{ mm}$$

Although migration of the adjuster screw in its threaded bore or socket has been found to be highly unlikely, we prefer to use a resin patch on the thread to insure that such unintended migration does not occur.

The embodiment of FIG. 6 is similar to the one already described except that a follower 20 is carried by the inner end of adjuster screw 19' and the adjuster screw has no enlarged head portion. We have also contemplated and have made an embodiment wherein the screw housing opens anteriorly and the hinge controls flexion; however, the clinical indications for such a hinge are virtually non-existent. We have also contemplated and have reduced to practice an embodiment in which the screw housing is anterior and the hinge controls extension.

While in the foregoing we have disclosed embodiments of the invention in considerable detail for purposes of illustration, it will be understood by those skilled in the art that many of these details may be varied without departing from the spirit and scope of the invention.

We claim:

1. An adjustable bi-pivotal hinge assembly comprising a hinge body including a pair of side plates with spaced opposing inner surfaces; first and second hinge arms having a pair of proximal end portions received between opposing inner surfaces of said side plates; pivot means pivotally connecting said hinge arms and said hinge body for independent movement of said arms between positions of flexion and extension about a pair of parallel pivot axes; each proximal end portion having a planar abutment surface parallel with said pivot axes; said abutment surfaces of said first and second arms extending in a common plane, facing in the same direction, and being disposed in side-by-side relation, when said arms are aligned in positions of full extension; said hinge body also including a screw housing having a threaded bore with a longitudinal axis normal to the common plane of said abutment surfaces when said arms are in positions of full extension; and adjuster screw means threadedly received in said bore and engagable with both of said abutment surfaces for limiting the extension of said arms.

2. The assembly of claim 1 in which said opposing inner surfaces of said side plates extend along parallel planes; said axis of said threaded bore being parallel with said opposing surfaces and equidistant therefrom.

3. The assembly of claim 2 in which said axis of said threaded bore is equidistant from said pivot axes of said hinge arms.

4. The assembly of claim 1 in which the common plane of said abutment surfaces extends through both of said pivot axes when said arms are in positions of full extension.

5. The assembly of claim 1 in which said hinge body includes an anterior wall joining said side plates.

6. The assembly of claim 1 in which said hinge body has anterior and posterior ends; said anterior end facing generally in the direction of movement of said arms as they approach said positions of extension; said screw housing being provided at said posterior end.

7. The assembly of claim 1 in which said screw means includes a rounded end portion directly engagable with said abutment surfaces.

8. The assembly of claim 1 in which said screw means includes a follower carried by one end of said screw means and engagable with said abutment surfaces.

* * * * *